United States Patent [19]

Delatte et al.

[11] Patent Number: 5,392,943
[45] Date of Patent: Feb. 28, 1995

[54] CANISTER FOR SPECIMEN HOLDERS

[75] Inventors: Daniel Delatte, Saint Maur; Cornelis Klok, Noiseau, both of France

[73] Assignee: L'Air Liquide, Societe Anonyme pour l'Etude et l'Exploitation des Procedes Georges Claude, Paris, France

[21] Appl. No.: 166,841

[22] Filed: Dec. 15, 1993

[30] Foreign Application Priority Data

Dec. 22, 1992 [FR] France .............................. 92 15455

[51] Int. Cl.6 ........................ B65D 25/00; F25B 19/00
[52] U.S. Cl. ................................. 220/475; 62/51.1;
62/64; 62/89; 62/373; 62/374; 62/457.1;
220/336; 220/740
[58] Field of Search .................... 422/99, 102, 104;
62/51.1, 64, 89, 373, 374, 372, 457.1; 220/740,
741, 336, 475

[56] References Cited

U.S. PATENT DOCUMENTS

| | | | |
|---|---|---|---|
| 1,473,162 | 11/1923 | Sage | 220/336 |
| 2,145,212 | 1/1939 | Edwards et al. | 220/336 X |
| 2,156,837 | 5/1939 | Bradbury | 220/336 |
| 2,543,107 | 2/1951 | Haatvedt | 220/336 X |
| 3,187,937 | 6/1965 | Berta | 220/751 |
| 3,323,755 | 6/1967 | Voitas et al. | 220/336 X |
| 3,352,445 | 11/1967 | Cochin | 220/336 X |
| 3,666,135 | 5/1972 | Kindle | 220/336 X |
| 3,707,079 | 12/1972 | Hawker | 62/189 |
| 4,314,450 | 2/1982 | Pelloux-Gervais | 62/51.1 |
| 5,035,344 | 7/1991 | Christopher | 220/336 |
| 5,321,955 | 6/1994 | Leonard | 62/51.1 |

FOREIGN PATENT DOCUMENTS 0026691 4/1981 European Pat. Off. .

*Primary Examiner*—Jill A. Warden
*Attorney, Agent, or Firm*—Young & Thompson

[57] ABSTRACT

A canister for specimen holders, includes a receptacle (1) having an upper opening (50) and a rod (3) for supporting the receptacle. A cover (5), supported on a support (8) mounted on the rod (3), is displaceable between a first position, over the opening (50) and a second position freeing the opening. The support (8) is mounted by hooking (10, 11) on the rod (3). A manually releasable lock (18) releasably locks the cover (5) in its first position. The cover (5) is pivotally mounted on the support (8) about a pivot (14) whose axis is parallel to the rod (3).

12 Claims, 2 Drawing Sheets

5,392,943

CANISTER FOR SPECIMEN HOLDERS

FIELD OF THE INVENTION

The present invention relates to canisters adapted to contain test tubes or specimen holders so as to maintain them within a receptacle filled with a cryogenic liquid, of the type comprising a receptacle having an upper opening and a rod for handling and gripping.

BACKGROUND OF THE INVENTION

A canister of this type is described in the document EP-A-0.026.691, in the name of the applicant.

The preservation of numerous products and biological specimens, particularly in the form of thin closed tubes called "specimen holders", of a usual capacity varying between 0.25 and 0.5 $cm^3$, is effected by immersing these holders in insulated receptacles, typically double walled, filled with a cryogenic liquid, typically liquid nitrogen. These receptacles have a capacity which can vary from 1 liter to more than 1000 liters and contain a variable number of holders, from about fifty to more than a million. The holders are not introduced in bulk into the receptacles but are grouped in intermediate containers called "canisters", according to the present invention, which can contain a number of holders varying from 50 to about 2000, according to the dimensions of the holders and the canisters.

When a canister, first loaded with specimen holders, is introduced into a receptacle filled with cryogenic liquefied gas, this latter penetrates the canister through its lower perforated end and can, if the canister is rapidly immersed in the liquid, lead to a substantial raising of the specimens relative to the canister with the risk of their leaving the canister by the upper end and being dispersed in the liquid in the receptacle. Moreover, it is desirable to emplace rapidly the canister in the bath of liquefied gas to avoid losses of cold and excessive vaporization of this latter.

SUMMARY OF THE INVENTION

The present invention has for its object to provide a canister structure permitting rapidly immersing the canister in a cold preservation liquid without risk of escape of the specimen holders from the canister.

To do this, according to one characteristic of the invention, the canister comprises a cover supported by a support mounted on the rod and displaceable between a first position, a so-called closure position, over the opening, and a second position exposing the opening.

According to other characteristics of the invention:
the cover support is mounted by hooking on the rod;
it is provided with manually unlockable means, for blocking the cover in its first position;
the cover is pivotally mounted on the support about a pivot axis parallel to the rod and preferably mounted in a first lateral end of the support.

With this arrangement, the cover can be easily placed in its second position for loading the specimen holders into the canister or withdrawing them from this latter, after which the cover is also easily placed in its so-called closed position, over the opening of the receptacle, above this latter and above the protruding ends of the specimen holders which it thus maintains in place within the receptacle while permitting the passage of the gas or liquid into the receptacle and out of the latter. The cover thus has no sealing function and simply ensures the retention function of the specimen holders within the receptacle. The length of the specimen holders and the diameter/height ratio of the receptacle prevent the specimen holders from making a large angle with the axis of the canister and it therefore suffices that the cover overlie laterally only a little beyond the dimensions of the upper opening of the canister.

BRIEF DESCRIPTION OF THE DRAWINGS

Other characteristics and advantages of the present invention will become apparent from the following description of an embodiment given by way of example but not at all limiting, with respect to the accompanying drawings, in which.

DETAILED DESCRIPTION OF THE INVENTION

Figure 1:
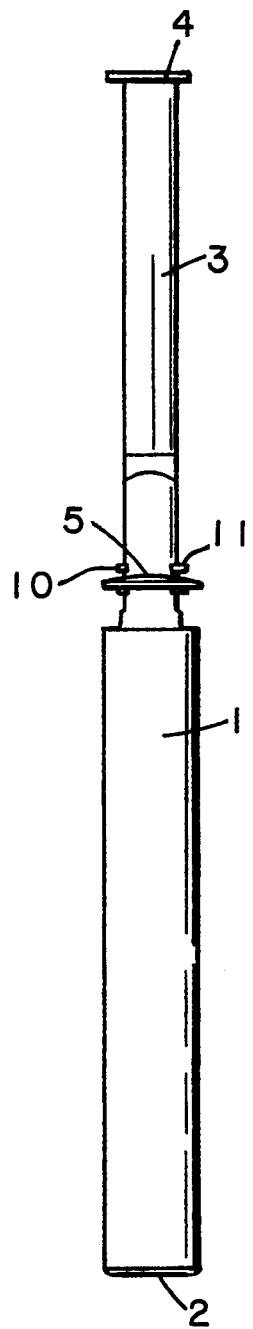
FIG. 1 is an assembly view, in elevation, of a canister according to the invention with the cover in closed position.
Figure 2:
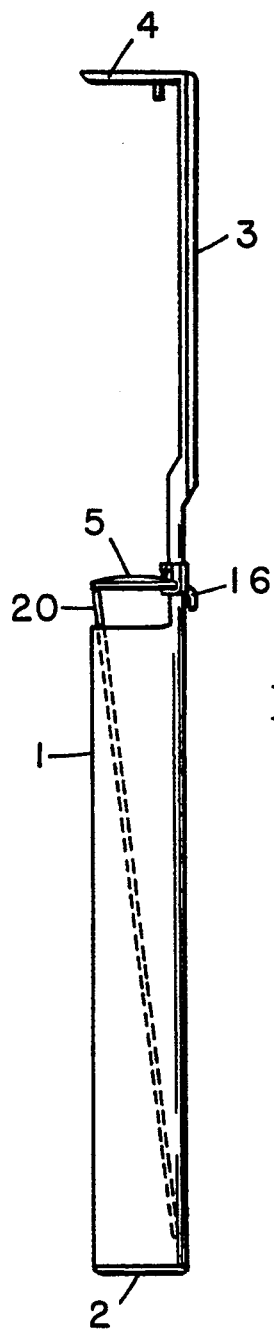
FIG. 2 is another view in elevation in a direction perpendicular to that of FIG. 1.
Figure 3:
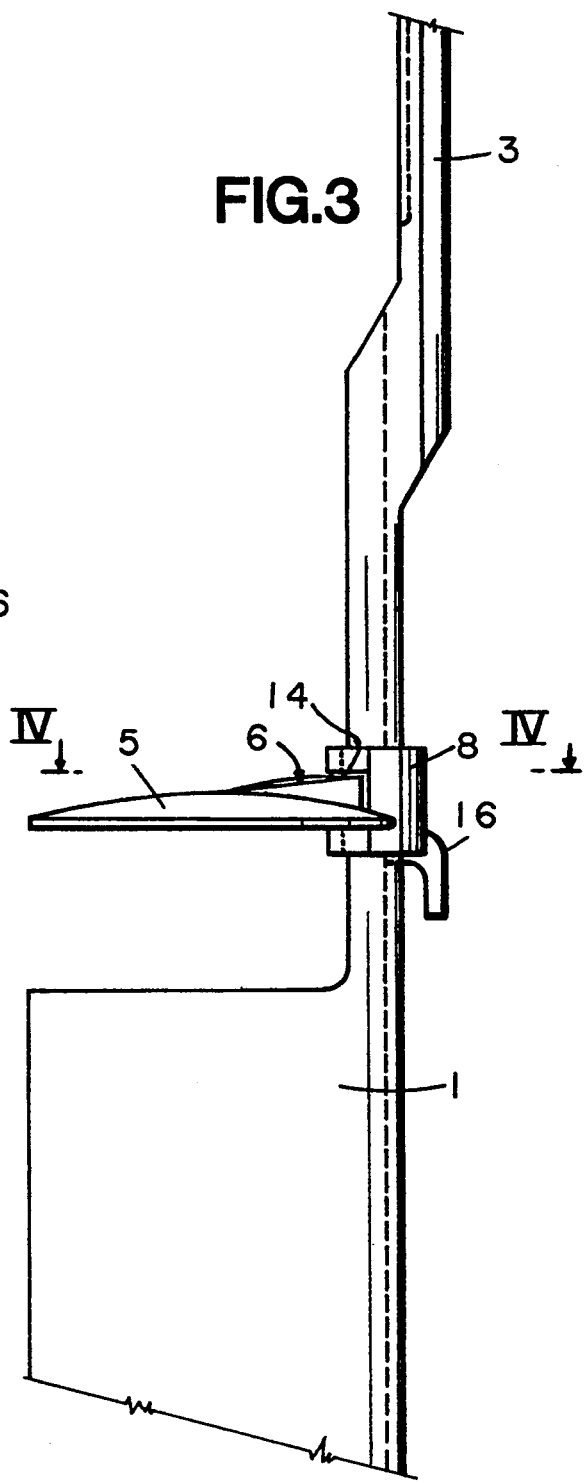
FIG. 3 is a detailed view of the canister and of the cover, corresponding to an enlargement of the central portion of FIG. 2.

There will be seen in FIGS. 1 to 3 a canister comprising an elongated receptacle 1, typically of tubular shape, whose bottom is closed by a pierced or perforated plate 2 and which is prolonged upwardly by a rod or tongue 3 provided, at its upper end, with a transverse tongue 4 for hooking of the canister in the neck of a cryobiological receptacle. The receptacle 1 and the rod 3, as well as if desired the bottom 2, are preferably made of a single piece of plastic material, they can however be constituted by metallic elements assembled for example by welding.

According to the invention, on the lower part of the rod 3 is mounted, by means of a support 8, a cover 5 having a general appearance of an upwardly convex disc, of a diameter slightly greater than the diameter of the upper opening 50 of the receptacle 1. The cover 5 and the support 8 are preferably of an elastic or semi-rigid plastic material. The upper surface of the cover 5 comprises a substantially radial rib 6 which extends beyond the periphery of the disc 5 and whose outer end is traversed by a through hole 7.

Figure 4:
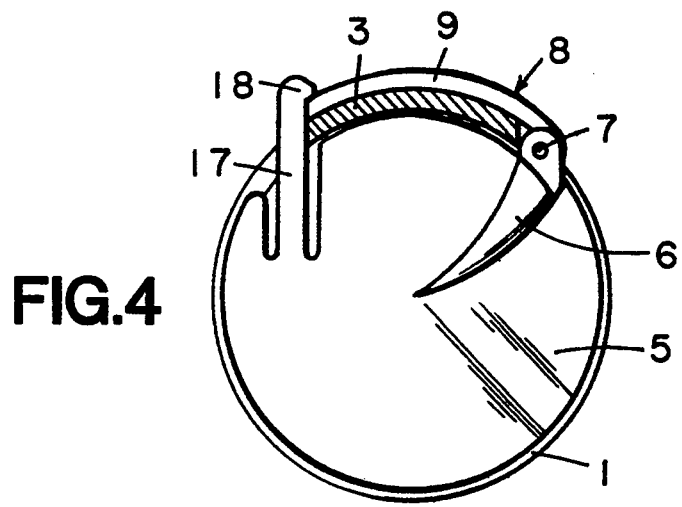
FIG. 4 is a cross-sectional view on the line IV—IV of FIG. 3.
Figure 5:
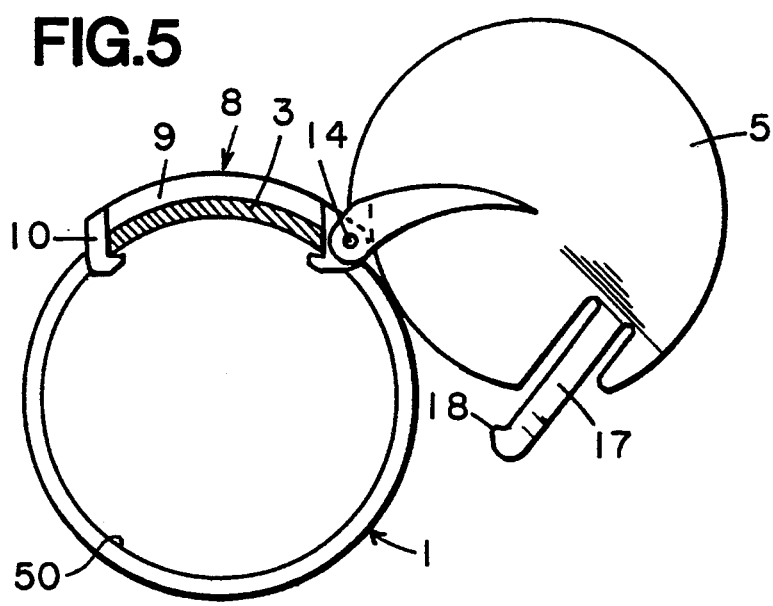
FIG. 5 is a view analogous to that of FIG. 4 but with the cover in open position.
Figure 6:
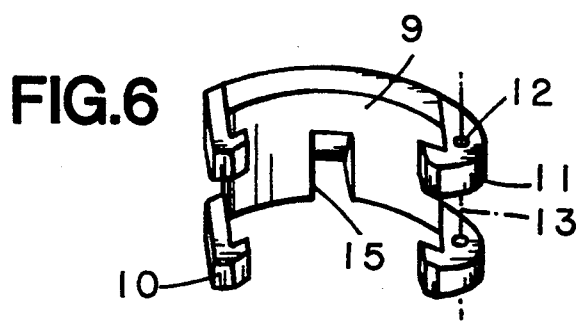
FIG. 6 is a perspective view of the cover support of FIGS. 1 to 5.

As better seen in FIGS. 4 to 6, the support 8 comprises a body 9 so shaped as to match the shape of the external surface of the rod 3, which typically has an arcuate shape. In the illustrated embodiment, the horizontal dimensions of the body 9 are substantially equal to those of the base of the rod 3 and the body is formed at each of its lateral opposite ends with at least one, typically two hooks 10, 11, directed toward the concavity of body 9 and arranged to come into engagement with the edges of the rod 3 while imprisoning this latter. On one of the sides of the body 9, the hooks 11 are enlarged and traversed by a bore 12 of common vertical axis 13. The vertical space between the hooks 11 is very slightly greater than the thickness of the external end of the rib 6 and the diameter of the bores 12 is the same as that of the passage 7 for the mounting of a pivot 14 constituting a hinge with a vertical axis for the cover relative to the support 8 and hence for the canister. The base of the body 9 of the support 8 preferably has a notch 15 which coacts, in the position of mounting the cover on the canister, with a projection 16 normally provided on the external surface of the rod 3, so as to ensure an easy and stable emplacement of the support 8 on the rod 3.

As is seen best in FIGS. 4 and 5, the cover 5 is preferably shaped to constitute a hooking tongue 17 projecting outwardly and terminating in a hook 18 arranged to hook itself resiliently over the rear edge of the lateral end of the support 8 opposite the pivot 14 when the cover 5 is in fully closed position, as shown in FIG. 4. To facilitate the manipulation of the cover 5, particularly to disengage resiliently the hook 18 so as to bring the cover 5 into its open position shown in FIG. 5, the margin of the cover 5 adjacent the hooking tongue 17 (to the left of FIG. 4)is preferably provided with indentations permitting its manipulation with gloves. The displacement of the cover 5 towards its closed position is effected simply by pushing laterally on the edge of cover 5 opposite the hooking tongue 18, the hooking taking place automatically after freeing, by the hook 18, of the lateral edge of the body 9 of support 8.

In FIG. 2, there is shown schematically a specimen holder 20 disposed in the receptacle 1 with the maximum inclination that it can attain when the cover 5 is closed, relative to the axis of the receptacle. It will be seen that even if the cover 5 has a diameter nearly equal to that of the upper opening 50 of the receptacle 1, the specimen holder cannot escape, even when the canister is plunged abruptly into the liquid mass.

Although the present invention has been described with respect to a particular embodiment, it is not thereby limited but is on the contrary susceptible to modifications and variations which will be apparent to one skilled in the art.

What is claimed is:

1. In a canister assembly for holding specimen holders in a low temperature environment, comprising a canister having an upper end formed with an access opening, a lower perforated end and a handling and supporting rod extending upwardly from a side portion of said upper end, the improvement comprising a support member carried by the rod and a cover hingedly supported on the support member, said cover being displaceable between a first position facing the access opening, and at least a second position freeing the access opening.

2. The assembly of claim 1, wherein said cover includes releasable locking means for releasably locking the cover in said first position.

3. The assembly of claim 1, wherein said support member is mounted onto the rod.

4. The assembly of claim 3, wherein said rod carries a projection forming an abutment for the support member.

5. The assembly of claim 1, wherein said cover comprises a rib portion and a side pivot member journalled within a first side end of the support member.

6. The assembly of claim 5, wherein said pivot is substantially perpendicular to the rib portion.

7. The assembly of claim 6, wherein said cover further comprises a resilient tongue extending outwardly and cooperating in releasable locking engagement with a second side end of the support member laterally spaced from said first side end.

8. The assembly of claim 5, wherein the support member is mounted onto the rod.

9. The assembly of claim 8, wherein the support member is made out of a plastic material.

10. The assembly of claim 1, wherein the cover is made out of a plastic material.

11. The assembly of claim 9, wherein the cover and the pivot member are integral and formed out of a plastic material.

12. The assembly of claim 10, wherein the cover is formed with an outer protrusion for facilitating its manipulation.

* * * * *